(12) United States Patent
Herrema et al.

(10) Patent No.: US 7,579,176 B2
(45) Date of Patent: Aug. 25, 2009

(54) METHOD FOR THE PRODUCTION OF POLYHYDROXYALKANOIC ACID

(75) Inventors: Markus Herrema, Laguna Niguel, CA (US); Kenton Kimmel, Dana Point, CA (US)

(73) Assignee: Newlight Technologies, LLC, Long Beach, CA (US)

( * ) Notice: Subject to any disclaimer, the term of this patent is extended or adjusted under 35 U.S.C. 154(b) by 65 days.

(21) Appl. No.: 11/676,928

(22) Filed: Feb. 20, 2007

(65) Prior Publication Data

US 2007/0202581 A1 Aug. 30, 2007

Related U.S. Application Data

(63) Continuation-in-part of application No. PCT/US2005/047415, filed on Dec. 29, 2005, said application No. 11/676,928 and a continuation-in-part of application No. 11/208,808, filed on Aug. 22, 2005, is a continuation-in-part of application No. 10/687,272, filed on Oct. 15, 2003, now Pat. No. 6,982,161.

(60) Provisional application No. 60/721,938, filed on Sep. 29, 2005, provisional application No. 60/603,857, filed on Aug. 24, 2004.

(51) Int. Cl.
*C12P 7/42* (2006.01)
*C12P 7/44* (2006.01)
*C12N 9/02* (2006.01)
*A62D 3/02* (2007.01)

(52) U.S. Cl. ......................... 435/146; 435/142; 435/189; 435/262.5

(58) Field of Classification Search .................. 435/146, 435/142, 189, 262.5
See application file for complete search history.

(56) References Cited

U.S. PATENT DOCUMENTS

| | | | |
|---|---|---|---|
| 3,878,305 | A | 4/1975 | Damico et al. |
| 4,375,515 | A | 3/1983 | Patel et al. |
| 4,524,569 | A | 6/1985 | Hanna |
| 5,344,766 | A | 9/1994 | Ramachandran et al. |
| H1430 | H | 4/1995 | Apel et al. |
| 5,434,062 | A | 7/1995 | Groleau et al. |
| 5,480,794 | A | 1/1996 | Peoples et al. |
| 5,487,834 | A | 1/1996 | Carman et al. |
| 5,642,630 | A | 7/1997 | Abdelmalek et al. |
| 5,727,903 | A | 3/1998 | Borray et al. |
| 5,747,584 | A | 5/1998 | Noda |
| 5,789,536 | A | 8/1998 | Liggat et al. |
| 5,842,357 | A | 12/1998 | Siwajek et al. |
| 5,849,894 | A | 12/1998 | Clemente et al. |
| 5,871,980 | A | 2/1999 | Naylor et al. |
| 5,942,597 | A | 8/1999 | Noda et al. |
| 6,043,063 | A | 3/2000 | Kurdikar et al. |
| 6,051,411 | A | 4/2000 | Turtakovsky et al. |
| 6,205,704 | B1 | 3/2001 | Schmitz et al. |
| 6,395,520 | B1 | 5/2002 | Babel et al. |
| 6,446,385 | B1 | 9/2002 | Crutcher |
| 6,599,423 | B2 | 7/2003 | Boles et al. |
| 6,666,027 | B1 | 12/2003 | Cardenas, Jr. |
| 6,709,849 | B2 | 3/2004 | Cheung |
| 6,749,368 | B2 | 6/2004 | Ankeny et al. |
| 6,770,464 | B2 | 8/2004 | Steinbuchel et al. |
| 6,982,161 | B1 | 1/2006 | Herrema |
| 7,098,298 | B2 | 8/2006 | Kinoshita et al. |
| 7,141,400 | B2 | 11/2006 | Yu |
| 7,455,999 | B2 | 11/2008 | Madison et al. |
| 2008/0160569 | A1 | 7/2008 | Ho et al. |
| 2008/0241886 | A1 | 10/2008 | Herrema et al. |

FOREIGN PATENT DOCUMENTS

| | | |
|---|---|---|
| WO | WO 2007/024255 | 3/2007 |
| WO | WO2008/103134 | 8/2008 |

OTHER PUBLICATIONS

Brigmon, Methanotrophic Bacteria: Use in Bioremediation, Westinghouse Savannah River Company, on-line publication No. WSRC-MS-2001-00058, http://sti.srs.gov/fulltext/ms2001058/ms2001058.html, 2001.*

Bioremediation—field Experience: Field Experience, Paul E. Flathman, Douglas E. Jerger and Jurgen H. Exner, CRC Press, Boca Raton, Florida, 1994, pp. 275-276.*

(Continued)

*Primary Examiner*—Karen Cochrane Carlson
*Assistant Examiner*—Rosanne Kosson
(74) *Attorney, Agent, or Firm*—Knobbe, Martens, Olson & Bear, LLP

(57) ABSTRACT

Embodiments of the invention relate to the microbial production of polyhydroxyalkanoic acids, or polyhydroxyalkanoates (PHA), from substrates which cannot be used as a source of carbon and/or energy for microbial growth or PHA synthesis and which have microbial and environmental toxicity. According to one embodiment of the invention, a process for the production of PHA is provided wherein an enzyme such as methane monooxygenase is used to convert volatile organic compounds into PHA through the use of microorganisms that are unable to use volatile organic compounds as a source of carbon for growth or PHA production.

22 Claims, 1 Drawing Sheet

OTHER PUBLICATIONS

Murrell et al., "Regulation of expression of methane monooxygenases by copper ions," Trends in Microbiology 8(5):221-225, 2000.*

Bartle, "Exploiting a Gaseating Bacteria," University of Bergen Magazine, 2002, at http://www.uib.no/elin/elpub/uibmag/en02/bacteria.html.

Cow Power, http://www.riverdeep.net/current/2002/03/032502t_cowpower.jhtml, Mar. 2002.

D'Aquino, "Methane to Protein," at http://www.aptagen.com/corporate/AptagenDocuments/Articles/che.html, Oct. 2000.

Gasser, "Agricultural productivity and the nitrogen cycle," Phil Trans R. Soc. Lond. B296:303-314, 1982.

Johnson et al., "Methane emissions from cattle," J. Anim. Sci. 37:2483-2492, 1995.

Polakovic, "Getting the Cows to Cool It," Los Angeles Times, Jun. 7, 2003, pp. A1-A17, Los Angeles, CA U.S.A.

Wendlandt et al., "Producing poly-3-hydroxybutyrate with a high molecular mass from methane," J. Biotechnol. 2001, vol. 86, pp. 127-133, see pp. 127-128.

Gay, S.W., "Natural ventilation for freestall dairy barns," Pub. No. 442-763, Virginia Cooperative Extension, Virginia Polytechnic institute and State university, http://www.ext.vt.edu/pubs/bse/442-763/442-763.pdf, 2002.

Climate Change 2001: Working Group I: The Scientific Basis, Intergovernmental Panel on Climate Change, http://www.grida.no/climate/ipcc_tar/wg1/017.htm, 2001.

Meeting Minutes of Methane to Markets, Agriculture Task Force Meeting dated Jun. 22, 2005. http://www.methanetomarkets.org/resources/ag/docs/ag-meeting.pdf.

Methane Emissions from Livestock Enteric Fermentation (p. 150). Reducing Emissions of Non-CO2 Greenhouse Gases (Sep. 2006). http://www.climatetechnology.gov/stratplan/final/CCTP-StratPlan-Ch07-Sep-2006.pdf.

How can livestock methane emissions be reduced? Ruminant Livestock (Mar. 2007). http://www.epa.gov/methane/rlep/faq.html.

The abatement challenge for Australian Agriculture (2007). Enteric methane (p. 2). http://www.dpc.vic.gov.au/CA256D800027B102/Lookup/Forum1EckardPaper/$file/Eckard%2017%20August%202007%20-%20The%20abatement%20challenge%20for%20agriculture.pdf.

5—Potential management practices and technologies for reducing methane emissions from agriculture. http://www.maf.govt.nz/mafnet/rural-nz/sustainable-resource-use/climate/green-house-gas-migration/ghg-mitigation-05.htm.

Technologies for Reducing Non-Energy-Related Emissions (Mar. 2006). Enteric Fermentation (p. 8). http://www.cfses.com/documents/climate/10_%20Jolley_Technologies_for_Reducing_Non-energy_Related_Emissions.pdf.

Matter 2.0 (Jul. 1999). 5.1.1 Enteric fermentation (p. 22). ftp://ftp.ecn.nl/pub/www/library/report/1999/c99048.pdf.

Nichols, Peter D., and White, D.C., "Accumulation of poly-B-hydroxybutyrate in a methane-enriched, halogenated hydrocarbon-degrading soil column: implications for microbial community structure and nutritional status". Hydrobiologia 1989, 176/177:369-377.

International Search Report and Written Opinion of PCT Application No. PCT/US05/47415.

International Preliminary Report on Patentability of PCT Application No. PCT/US05/47415.

Co-Pending U.S. Appl. No. 11/208,808, filed Aug. 22, 2005. Title: Process for the Utilization of Ruminant Animal Methane Emissions.

Gooch, Curt A., Natural or Tunnel Ventilation of Freestall Structures: What is Right for Your Dairy Facility? www.milkproduct.com, Published Nov. 4, 2005.

Tyson, John T. et al., Tunnel Ventilation for Tie Stall Dairy Barns, Penn State, College of Agricultural Sciences, Agricultural and Biological Engineering, 2nd Edition Jan. 1, 2004.

* cited by examiner

US 7,579,176 B2

METHOD FOR THE PRODUCTION OF POLYHYDROXYALKANOIC ACID

RELATED APPLICATIONS

This application is a continuation-in-part of PCT Application No. US05/47415, filed Dec. 29, 2005, which claims the benefit of Provisional Application No. 60/721,938, filed Sep. 29, 2005; this application is also a continuation-in-part of co-pending patent application Ser. No. 11/208,808, filed Aug. 22, 2005, which is a continuation-in-part of patent application Ser. No. 10/687,272, filed Oct. 15, 2003, now issued as U.S. Pat. No. 6,982,161, and claims the benefit of Provisional Application No. 60/603,857, filed Aug. 24, 2004, all incorporated by reference herein.

BACKGROUND OF THE INVENTION

1. Field of Invention

This invention relates generally to the production of polyhydroxyalknoic acids, specifically to the microbial production of polyhydroxyalkanoates (PHA) from substrates which are bacteriocidal and which cannot be used as a source of carbon for growth or PHA production.

2. Description of the Related Art

Polyhydroxyalkanoates (PHAs) are polymers generated by microorganisms as energy storage vehicles. PHAs are biodegradable and biocompatible polymers that can be used as alternatives to petrochemical-based plastics such as polypropylene, polyethylene, and polystyrene. In comparison to petrochemical-based plastics, which are not biodegradable, PHA plastics afford significant environmental benefits.

Despite the advantages of using PHA plastics, the high price of PHAs compared to the low price of petrochemical-based plastics have significantly limited their widespread use. PHAs are commercially produced in bacterial fermentation processes wherein a carbon substrate is used to drive microorganism growth and PHA synthesis. Since carbon is used in significant quantities in the PHA synthesis process, carbon inputs largely determine the overall price of PHA. Accordingly, in order to make PHA competitive with petrochemical-based polymers, there is a significant need to develop novel sources of carbon for PHA synthesis.

Prior to the applicants' discovery, it was believed that carbon substrates used to produce PHA were limited to substrates that could be used by microorganisms as a source of carbon for growth, such as sugar or high fructose corn syrup. Since carbon forms the backbone of the PHA molecule and the cellular structures required to enable intracellular PHA synthesis, in the past, substrates that could not be used by microorganisms as a source of carbon for cellular growth or PHA synthesis, or carbon-based substrates that were either growth-limiting or growth-inhibiting, that is, bacteriostatic or bacteriocidal, respectively, were not considered useful for the PHA production process.

In U.S. Pat. No. 6,395,520, Babel, et al., herein incorporated by reference in its entirety, disclose a PHA production method for the use of substrates that exhibit the phenomenon of substrate inhibition, but only in cases of excess substrate, wherein the capacity of microorganisms to use the carbon within substrates for PHA production is determined by substrate concentration. The microorganisms described by Babel, et al. are metabolically capable of using particular substrates as a source of carbon for growth and PHA synthesis as long as the concentrations of those substrates are sufficiently low. Babel, et al. do not disclose a method for the use of substrates that cannot be used at all by PHA-producing microorganisms as a source of carbon for growth or PHA synthesis at any concentration, including at very low concentrations.

Volatile organic compounds (VOCs) are compounds that form gaseous vapors under normal atmospheric pressures and temperatures and engage in photochemical reactions to form oxidized photochemicals. VOCs contribute heavily to the formation of tropospheric pollutants such as ozone and smog, and human exposure to airborne volatile organic compounds is known to cause a variety of adverse health effects, including liver damage, brain damage, and cancer. VOCs are considered to represent one of the most important classes of soil, air, and groundwater pollutants in the United States. VOCs, are emitted by a wide range of industrial processes, including paint manufacturing, chemical synthesis, and wastewater chlorination. VOCs, which, as used herein, excludes methane in some embodiments, cannot be oxidized into non-toxic compounds or used as growth substrates by most naturally-occurring microorganisms, and subsequently persist in the environment as highly recalcitrant pollutants.

SUMMARY OF THE INVENTION

Embodiments of the present invention relate to a novel method for the production of PHA through the use of bacteriocidal, bacteriostatic, or otherwise inhibiting VOCs as a source of carbon.

Prior to the applicants' invention, no methods were known to the applicant for the production of PHA from substrates which could not be assimilated as a source of carbon at any concentration and which simultaneously represented growth-inhibiting agents. Prior to the applicants' discovery, such substrates were considered non-useful as a source of carbon for the production of PHA.

It has now been found that, as an alternative to growth-promoting carbon substrates, PHAs can also be produced from substrates which cannot be metabolically assimilated as a source of carbon for growth or PHA synthesis at any concentration and which exhibit toxic and metabolism inhibiting effects at all concentrations. Thus, the process according to one embodiment of the invention uses a traditionally toxic source of carbon typically discharged as environmentally hazardous industrial waste for the production of PHA in a novel system comprising microorganisms which are metabolically incapable of using the carbon contained within such substrates for either growth or PHA synthesis.

Prior to the applicant's invention, non-methane VOCs, hereinafter used interchangeably with the term VOCs, were not considered useful as a source of carbon for the production of polyhydroxyalkanoates. In particular, VOCs are toxic to most microorganisms capable of accumulating PHAs in high volumes, and no microorganisms currently used to produce PHAs in large volumes are able to use the carbon within VOCs for PHA synthesis. Moreover, many VOCs are found in material streams comprising a range of VOCs that cumulatively form a highly toxic substrate to even the most robust microorganisms that might be capable of using one specific specie of VOC, such as benzene, for growth. Accordingly, VOCs, prior to the applicant's discovery were not considered a viable source of carbon for PHA production.

Prior to the applicant's invention, no methods were known to the applicant to use VOCs to create PHA, and, specifically, no methods were known to use VOCs to create PHA through the use of microorganisms that are unable to use VOCs as a source of carbon for growth or PHA production. In light of the economic and environmental advantages of using the carbon contained within VOCs for the production of PHAs, there exists a significant need for a method to use VOCs as a viable carbon substrate for the production of PHAs, particularly in a system wherein VOCs are bacteriocidal and cannot be used as a source of carbon for growth and/or PHA production. Additionally, there exists a significant need for a method to produce PHA though the simultaneous use of two or more VOCs.

According to one embodiment of the present invention, the applicant has discovered that as an alternative to traditional growth substrates such as glucose and vegetable oils, PHAs can be produced from VOCs that are growth inhibiting substrates to one or all of the microorganisms used in the PHA production process, at any VOC concentration. Thus, the process according to one embodiment of the invention uses environmentally toxic VOCs as cost-effective sources of carbon for PHA production, enabling the disposal of hazardous substances while simultaneously synthesizing useful materials.

Methane-oxidizing, or methanotrophic, microorganisms are well known for their capacity to use methane as their sole source of carbon for growth. In order to catalyze the oxidation and subsequent metabolism of methane, methanotrophic microorganisms typically employ an enzyme called methane monooxygenase (MMO), which is intracellularly produced in either particulate or soluble form (pMMO or sMMO, respectively). While sMMO is able to catalyze the oxidation of a wider range of non-methane volatile organic compounds than pMMO, pMMO is also able to catalyze the oxidation of many volatile organic compounds. Methanotrophic microorganisms are unable to use volatile organic compounds as a source of either carbon or energy, and as such volatile organic compounds that are oxidized by methanotrophic microorganisms engender growth-inhibiting effects by temporarily or permanently disabling the MMO molecule that is essential for the continued life of the methanotrophic microorganism.

Since the oxidation of VOCs by methanotrophic microorganisms through the use of methane monooxygenase is a growth-inhibiting action, and since methanotrophic microorganisms, according to some embodiments of the invention, are unable to use volatile organic compounds as a source of carbon for either growth or PHA synthesis, the use of VOCs and methanotrophic microorganisms for the production of PHA was not considered a viable method for PHA production prior to the applicant's discovery.

Prior to the applicant's invention, no methods were known to applicant to use VOCs to produce PHA in a controlled biological system wherein VOCs cannot be used as a source of carbon for either growth or PHA production, and no methods were known to applicant to use methanotrophic microorganisms to incorporate the carbon within toxic volatile organic compounds into PHA. Consequently, VOCs remain a significant source of environmental degradation and wasted carbon.

Several embodiments of the present invention relate to a novel method for the production of PHA through the use of bacteriocidal VOCs as a source of carbon.

In one embodiment of the invention, a method for the microbial production of PHA from VOCs which act as bacteriocidal and/or bacteriostatic agents and which cannot be used as a source of carbon for microorganism growth or PHA production is provided.

According to another embodiment of the invention, one or more VOCs are used for the production of PHA wherein methane-oxidizing microorganisms use an enzymatic catalyst in the form of methane monooxygenase (MMO) to produce extracellular MMO-oxidized VOCs which are simultaneously contacted with microorganisms that are able to synthesize PHA using the MMO-oxidized VOCs as a source of carbon, wherein the PHA-synthesizing microorganisms are caused to use the carbon contained within the MMO-oxidized VOCs for the production and accumulation of PHA.

In one preferred embodiment of the invention, one or more VOCs that can be oxidized by methane monooxygenase (MMO) are fed into a reactor comprising i) microorganisms synthesizing the MMO enzyme, ii) microorganism growth medium, and iii) PHA-synthesizing microorganisms that have the capacity to use the MMO-oxidized form of the VOCs for growth and PHA synthesis, wherein the VOCs are converted into the MMO-oxidized form of the VOCs through the action of the methane monooxygenase, and the PHA-synthesizing microorganisms are caused to use the carbon contained with the MMO-oxidized VOCs for PHA production.

In one embodiment of the invention, a process for the production of a PHA from one or more VOCS is provided. In one embodiment, the method comprises providing one or more VOCs and providing one or more methane-oxidizing microorganisms capable of oxidizing the VOCs to produce an oxidized compound. In one embodiment, the methane-oxidizing microorganisms do not use at least one or any of the VOCs as a source of carbon or energy. In one embodiment, the VOCs inhibit the growth of the methane-oxidizing microorganisms, and is thereby metabolically toxic. The method further comprises providing the PHA-synthesizing microorganisms capable of incorporating a carbon contained within the oxidized compound into a PHA material. A growth-culture medium that regulates the metabolism of the methane-oxidizing microorganisms and the PHA-synthesizing microorganisms is provided. The method further comprises mutually exposing the VOCS, methane-oxidizing microorganisms, and growth-culture medium, thereby causing or allowing the methane-oxidizing microorganisms to convert the VOCS into the oxidized compound. PHA-synthesizing microorganisms are contacted with the oxidized compound. The method further comprises manipulating the growth culture medium to cause or allow the PHA-synthesizing microorganisms to use the carbon contained within the oxidized compound for the production of the PHA material, thereby, according to one embodiment, using a metabolically toxic, growth-inhibiting VOC to produce the PHA material. The PHA material may then be harvested.

In another embodiment, a process for the production of a PHA from one or more VOCs comprises exposing the methane-oxidizing microorganisms to methane prior to exposing the methane-oxidizing microorganisms to the VOCS to encourage growth of the methane-oxidizing microorganisms.

In one embodiment, the VOCs inhibit the growth of methane-oxidizing microorganisms by temporarily or permanently deactivating the enzymes, such as methane monooxygenase, required to metabolize methane.

In another embodiment, the VOCs inhibit the growth of methane-oxidizing microorganisms by exhibiting bacteriocidal or bacteriostatic activity, such as the ability to slow or stop reproduction, the ability to destroy or kill, or the ability to hamper or prevent growth of microorganisms.

In one embodiment, methane-oxidizing microorganisms comprise a naturally-occurring or genetically-engineered microorganism capable of oxidizing VOCs.

In one embodiment, methane-oxidizing microorganisms oxidize the VOCs using methane monooxygenase.

In another embodiment, the step of manipulating the growth-culture medium to cause or allow the PHA-synthesizing microorganisms to produce the PHA material comprises depleting an essential growth nutrient.

In yet another embodiment, the step of manipulating the growth-culture medium to cause or allow the PHA-synthesizing microorganisms to produce the PHA material comprises reducing the concentration of compounds selected from the group consisting of the following: iron, oxygen, nitrogen, magnesium, potassium, phosphate, phosphorus, or copper.

In one embodiment, the PHA material comprises at least one carbon molecule derived from the oxidized compound, wherein the oxidized compound is the oxidized form of the VOCs.

In one embodiment, the mass of PHA material produced is about 5-80% of the mass of PHA-synthesizing microorganisms used to produce the PHA material. In some embodiments, the mass of PHA material produced is about 20-60%, 30-50%, or about 40% of the mass of PHA-synthesizing microorganisms. In one embodiment, the mass of PHA material produced is greater than 50% of the mass of PHA-synthesizing microorganisms used to produce the PHA material.

In one embodiment, the invention comprises altering the concentration of copper within the growth culture medium, thereby altering the substrate specificity of methane monooxygenase. In some embodiments, the substrate specificity is altered by causing the methane-oxidizing microorganisms to produce either particulate or soluble methane monooxygenase. In one embodiment, the invention comprises increasing the availability of copper to the methane-oxidizing microorganisms, thereby causing the methane-oxidizing microorganisms to produce particulate methane monooxygenase. In an alternative embodiment, the invention comprises decreasing the availability of copper to the methane-oxidizing microorganisms, thereby causing the methane-oxidizing microorganisms to produce soluble methane monooxygenase.

In one embodiment, the method comprises altering the copper concentration to cause a majority of the methane-oxidizing microorganisms to produce particulate methane monooxygenase, thereby narrowing the range of the VOCs that can be oxidized by the methane-oxidizing microorganisms. In another embodiment, the invention comprises altering the copper concentration to cause a majority of the methane-oxidizing microorganisms to produce soluble methane monooxygenase, thereby widening the range of the VOCs that can be oxidized by the methane-oxidizing microorganisms. In other embodiments, the concentration of iron is altered instead of or in addition to copper to affect the type of methane monooxygenase used, produced, or expressed. One of skill in the art will understand that alteration of other compounds that cause the methane-oxidizing microorganisms to produce a certain type of MMO can be used in accordance with several embodiments of the invention.

In one embodiment of the invention, a method for producing PHA from a VOC is provided. In one embodiment, the method comprises combining a methanotrophic microorganism comprising methane monooxygenase with a VOC, wherein the methanotrophic microorganism uses the methane monooxygenase to metabolize the VOC to produce a metabolized-VOC. The method further comprises combining the metabolized-VOC with a PHA-generating microorganism, wherein the PHA-generating microorganism uses at least one carbon molecule in the metabolized-VOC to produce PHA. In one embodiment, the method comprises inducing the PHA-generating microorganism to produce PHA by reducing the availability of at least one nutrient from a growth medium comprising the PHA-generating microorganism.

In one embodiment of the invention, a kit (system or collection of items for a common purpose) for the production of PHA from a VOC is provided. In one embodiment, the kit comprises methanotrophic microorganisms and/or enzymes that metabolize VOCs, PHA-generating microorganisms, a first growth medium, and a second growth medium. The second growth medium lacks compounds selected from the group consisting of the following: iron, oxygen, nitrogen, magnesium, potassium, phosphate, phorphorus, or copper. The second growth medium can be the first medium absent a nutrient, or can be an entirely new medium. The kit may further comprise instructions for contacting the methanotrophic microorganisms to the VOCS to produce an oxidized VOC, wherein the oxidized VOC is subsequently used as a source of carbon for the PHA-generating microorganisms to generate PHA upon introduction of the second growth medium.

In one embodiment, a system for the production of PHA is provided, wherein the system comprises methanotrophic microorganisms or engineered MMO, PHA-generating microorganisms, and one or more growth mediums. The system can optionally comprise one or more bioreactors.

In one embodiment, the invention comprises a PHA produced by any of the systems or methods described herein. In another embodiment, the invention comprises a PHA, wherein the PHA comprises a carbon from an oxidized non-methane VOC, and wherein the oxidized non-methane VOC is an oxidized product of a methane oxidizing microorganism. In one embodiment, at least one carbon molecule in the PHA is the same, substantially the same, or derived from, a carbon molecule in a non-methane VOC, and the oxidized form of that non-methane VOC. In yet another embodiment of the invention, a PHA material comprising a carbon molecule from a non-methane VOC is provided.

The PHA according to any of the embodiments described herein can be isolated and/or purified according to methods known in the art, including but not limited to, fractionation, dialysis, affinity isolation, sequential surfactant and hypochlorite treatment, and other mechanical or chemical isolation and/or purification techniques. In one embodiment, the PHA is separated from the cell components or other undesired substances by solvent extraction and aqueous digestion. Centrifugation, lyophilization, and chemical digestion with chemicals such as sodium hydroxide, chloroform, and methylene chloride may also be used. Fluid extraction using gases such as carbon dioxide may be used in according with several embodiments. Sonication, freeze-drying, homogenization and enzymatic digestion may be used to disrupt cells and liberate PHA. Other methods of dissolution and precipitation may also be used.

In one embodiment of the invention, a method for producing PHA from a VOC is provided. In one embodiment, the method comprises combining a methane oxidizing enzyme with a VOC, wherein the methane oxidizing enzyme oxidizes the VOC to produce an oxidized-VOC, and combining the oxidized-VOC with a PHA enzyme, wherein the PHA enzyme uses at least one carbon molecule in the oxidized-VOC to produce PHA. The methane oxidizing enzyme may comprise any enzyme produced by any methane-oxidizing microorganism that has the capacity to oxidize, in whole or in part, the methane and the VOCs, including but not limited to methane monooxygenase. The methane oxidizing enzyme may be associated with (e.g., be part of) a microorganism or may be independent. The methane oxidizing enzyme may comprise a synthetic or engineered substance or genetic sequence, or may be derived from a microorganism or other organism, and may be isolated and/or purified. The PHA enzyme may comprise any enzyme produced by any PHA-generating microorganism that has the capacity to generate, in whole or in part, PHA. The PHA enzyme may be associated with (e.g., be part of) a microorganism or may be independent. The PHA enzyme may comprise a synthetic or engineered substance or genetic sequence, or may be derived from a microorganism or other organism, and may be isolated and/or purified.

According to any of the embodiments described herein, PHA-generating microorganisms may comprise a synthetic or engineered substance or genetic sequence, or may be derived from a microorganism or other organism, and may be isolated and/or purified. For example, PHA polymerases or PHA synthases may used instead of or in addition to the PHA-generating microorganism. Examples of such PHA enzymes and methods that can be used in accordance with several embodiments described herein are described in U.S. Pat. No. 5,480,794, herein incorporated by reference in its entirety.

In one embodiment, methane-oxidizing microorganisms and PHA-generating microorganisms are used. In another embodiment, enzymes are used instead of the methane-oxidizing microorganisms. In yet another embodiment, enzymes are used instead of the PHA-generating microorganisms. In another embodiment, synthetic, engineered or isolated enzymes or catalysts (or structural or functional equivalents) are used in addition to methane-oxidizing microorganisms and/or PHA-generating microorganisms. In a further embodiment, the system is essentially free of methane-oxidizing microorganisms and PHA-generating microorganisms, and the method according to any of the embodiments described herein is carried out by synthetic, engineered or isolated enzymes or catalysts (or structural or functional equivalents).

According to any of the embodiments described herein, one or more VOCs are obtained from one or more of the following sources: landfill, wastewater treatment system, coal mine, natural gas system, agricultural waste management system, ruminant animal operation. Other sources may be used in accordance with embodiments of the invention.

According to any of the embodiments described herein, VOCs may comprise one or more of the following: vinyl chloride, benzene, butane, trichloroethylene, toluene, ethylbenzene, dichloromethane, trichloromethane, ethane, 1-2-dichloroethane, 1,1-dichloroethylene, chlorodifluoromethane, xylene, and other volatile organic compounds. In one embodiment, the VOC is a methane VOC.

According to any of the embodiments described herein, methane-oxidizing microorganisms include, but are not limited to, *Bacillus, Mycobacterium, Actinomyces, Nocardia, Pseudomonas, Methanomonas, Protaminobacter, Methylococcus, Arthrobacter, Brevibacterium, Acetobacter, Methylomonas, Acetobacter, Micrococcus, Rhodopseudomonas, Corynebacterium, Rhodopseudomonas, Microbacterium, Achromobacter, Methylobacter, Methylosinus*, and *Methylocystis*.

According to any of the embodiments described herein, PHA-synthesizing microorganisms comprise a naturally-occurring or genetically-engineering microorganism capable of using carbon from the oxidized compound to produce the PHA material.

According to any of the embodiments described herein, PHA-synthesizing microorganisms include, but are not limited to, *Alcaligenes, Acidovorax, Azotobacter, Bacillus, Brevibacillus, Pseudomonas, Ralstonia, Rhizobium*, and/or *Rhodobacter*.

According to any of the embodiments described herein, the growth-culture medium comprises one or more of the following: potassium, phosphorus, nitrogen, magnesium, sulfate, iron, cobalt, copper, dissolved oxygen, dissolved methane, dissolved VOCs, zinc, sodium, nickel, manganese, boron, water, microorganisms, and organic metabolites.

According to several embodiments described herein, methane VOCs (VOCs that comprise a methane chemical group) may be used instead of or in addition to VOCS.

Besides the objects and advantages already described, several preferred embodiments of the invention described herein will have one or more of the following advantages: the process i) converts a growth-inhibiting substrate into a useful source of carbon for PHA production, ii) converts an environmental toxin into a non-toxic and environmentally-friendly good, iii) creates useful goods in the form of biodegradable PHAs from a heretofore wasted and environmentally-damaging industrial byproduct, iv) uses a carbon-based material previously considered non-useful for PHA production, v) and may reduce the cost of PHA production while mitigating the negative potential environmental impact of volatile organic compounds, thereby increasing the economic viability of PHA plastics relative to petrochemical-based plastics.

Further objects and advantages will become apparent from a consideration of the ensuing description.

DETAILED DESCRIPTION OF THE PREFERRED EMBODIMENTS

Figure 1:
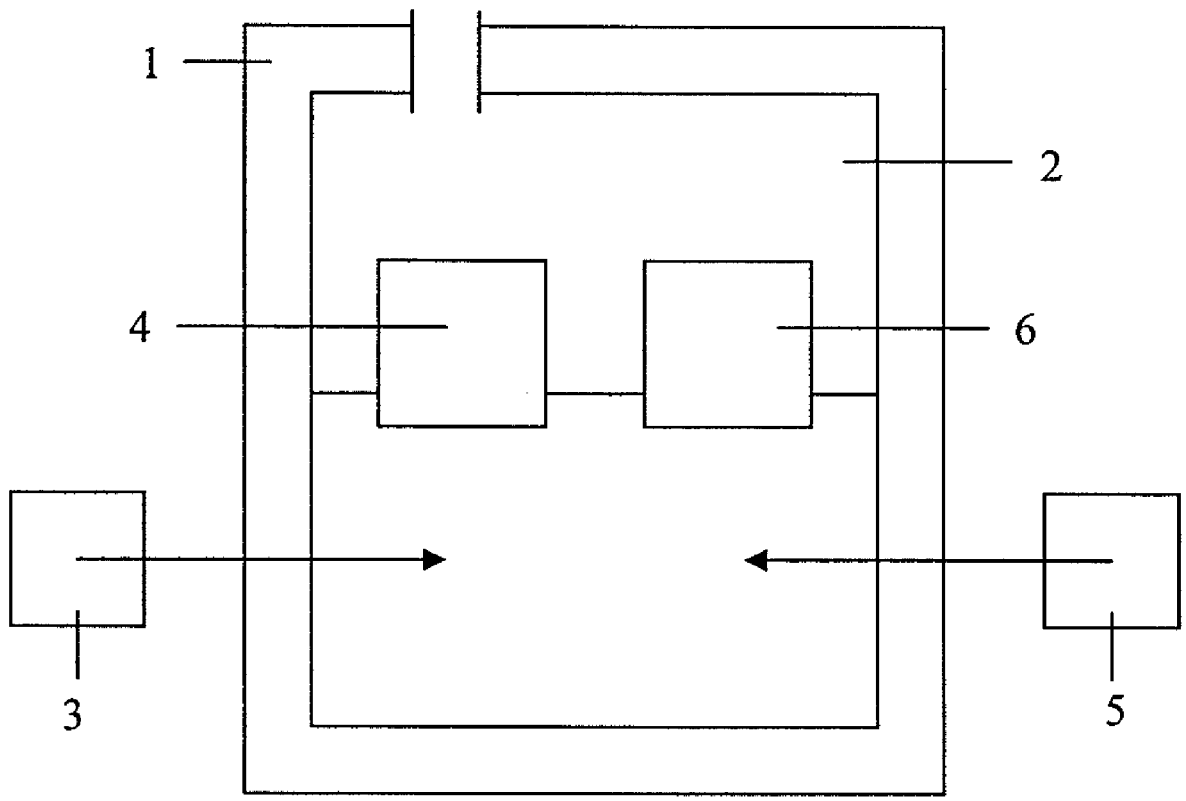
FIG. 1 shows a polyhydroxyalkanoate production system according to one embodiment of the invention.

While this invention is susceptible to embodiment in many different forms, there will herein be described in detail a preferred method of carrying out a process in accordance with the invention with the understanding that the present disclosure is to be considered as an example of the principles of the invention and is not intended to limit the broad aspect of the invention to the embodiments illustrated.

In a preferred embodiment of the invention, one or more VOCs that can be oxidized by methane monooxygenase (MMO) is introduced into a reactor comprising i) a microorganism growth medium, ii) microorganisms containing methane monooxygenase (hereinafter referred to as MMO microorganisms, which are available from culture collections) and iii) microorganisms that are able to use the carbon contained within the MMO-oxidized form of the VOC as a source of carbon for growth and PHA synthesis (hereinafter referred as PHA microorganisms), wherein the MMO microorganisms are caused to use methane monooxygenase to oxidize the VOC into a MMO-oxidized form of the VOC and transfer the MMO-oxidized VOC into the growth medium, wherein the PHA microorganisms are caused use the carbon contained within the MMO-oxidized VOC as a source of carbon for growth, and wherein, according to one embodiment of the invention, the growth conditions within the reactor are adjusted in order to cause the PHA microorganisms to use the carbon contained within the MMO-oxidized VOC for the production of PHA.

In one preferred embodiment of a method to carry out a process in accordance with the invention, as pictured in FIG. 1, bioreactor 1 is partially filled with growth medium 2 comprising water and growth nutrients. In one embodiment, the growth medium is liquid and comprises one or more minerals. In one embodiment, the bioreactor comprises about 0.7-1.5 g $KH_2PO_4$, 0.7-1.5 g $K_2HPO_4$, 0.7-1.5 g $KNO_3$, 0.7-1.5 g NaCl, 0.1-0.3 g $MgSO_4$, 24-28 mg $CaCl_2 \cdot 2H_2O$, 5.0-5.4 mg EDTA $Na_4(H_2O)_2$, 1.3-1.7 mg $FeCl_2 \cdot 4H_2O$, 0.10-0.14 mg CoCl2*6H2O, 0.08-1.12 mg MnCl2*2H2O, 0.06-0.08 mg ZnCl2, 0.05-0.07 mg H3BO3, 0.023-0.027 mg NiCl2*6H2O, 0.023-0.027 mg NaMoO4*2H2O, and 0.011-0.019 mg CuCl2*2H2O.

In one embodiment, the bioreactor is a chamber, vessel or container for bioprocessing or biological reactions. In some embodiments, the bioreactor is a steel, concrete, or plastic containment chamber, such as an open, partially-enclosed, or fully enclosed tank, such as a conical or square tank, which may or may not be preferentially attached to input lines for water, mineral media, microorganism culture, air, methane, VOCs, or other appropriate input. In some embodiments, two or more bioreactors are used. When two or more bioreactors are used, the bioreactors may be used for different steps of a process as described herein, or may be used for identical bioprocessing, thereby, in one embodiment, increasing the efficiency of the system.

In other embodiments, the bioreactor is a pressurized vessel, whereby the concentration of gases in liquids contained within the reactor can be adjusted, increased, decreased, or otherwise controlled. The tank may also be a pre-fabricated bioreactor. The tank may also be a plastic tank made from polyethylene, polypropylene, reinforced plastic, cross-linked polyethylene, or other suitable material. The height to diameter ratio of the tank may be increased or decreased to preferentially adjust the contact time of gases injected into the reactor. The tank may be vented. The headspace of the tank may also be placed under negative air pressure in order to prevent the absorption of carbon dioxide into materials within the bioreactor. The vessel may also be outfitted with means to reduce the concentration of carbon dioxide within various components, such as liquid mineral media, within the reactor. Means for reducing the concentration of carbon dioxide within the reactor may include air injection, alkaline injection, air stripping, or other suitable adjustment mechanism. The vessel may be continuously or batch monitored with appropriate equipment to measure parameters such as pH, dissolved oxygen, dissolved gases, dissolved nitrogen, dissolved phosphorus, turbidity, and/or PHA accumulation within microorganism cells. One or more bioreactors described in U.S. Pat. Nos. 6,844,187; 6,670,169; and 4,654,308, all herein incorporated by reference, can be used in accordance with several embodiments of the invention.

According to one embodiment, a combination of gases (e.g., air) 3 comprising 50% methane and 50% oxygen (by volume) is injected into the liquid portion of bioreactor 1. In other embodiments, the following mixture of gases can be used: methane in the range of about 1% to about 95%, and oxygen in the range of about 1% to about 95%. The gaseous mixture may also comprise methane in the range of about 30% to about 70%. The gaseous mixture may also comprise methane in the range of about 80-95%. The gaseous mixture may also comprise methane. The gaseous mixture may also comprise methane in the range of about 0.01% to 1%. The gaseous mixture may also comprise impurities, such as VOCs, in the range of about 0.01% to about 20%. In some embodiments, methane is used to cultivate microorganisms, and oxygen is added later for growth. The phrases "combination of gases" or "mixture of gases", as used herein, shall be given their ordinary meaning and shall refer to combinations, and mixtures interchangeably.

In one embodiment, one or more gases are provided into the bioreactor from/by using one or more suitable air injection mechanisms, such as an air pump, rotary air injection pump, diaphragm pump, air-operated diaphragm pump, electric diaphragm pump, or other suitable air conveyance mechanism in order to capture, convey, and/or inject gases into the bioreactor that can be obtained either as compressed gas, natural gas, compressed oxygen and/or methane gas, or gas emitted by landfills, wastewater treatment facilities, agricultural operations, coal mines, natural gas systems, and/or other suitable sources of methane emissions.

According to one embodiment, MMO microorganisms 4 are introduced to bioreactor 1 and propagated through the use of the methane within air 3 as a source of carbon for growth. In another embodiment of the invention, MMO microorganisms may be cultured separately from bioreactor 1, and then introduced into bioreactor 1 following such independent cultivation.

Soluble methane monooxygenase (sMMO) has the capacity to oxidize a wider range of non-methane organic compounds than particulate methane monooxygenase (pMMO), which has a more narrow substrate specificity. According to one embodiment, the maintenance of copper concentrations will be useful to effect the consistent production of either soluble or particulate methane monooxygenase. In particular, if the concentration of copper in medium 2 is minimized and kept below specific and well known concentrations, such as $5 \times 10^{-9}$ M or another appropriate concentration, the production of sMMO may be effected in most or all methanotrophic cells accessing that copper-limited medium 2. It will be useful, in some embodiments, to cause or allow most MMO microorganisms 4 in bioreactor 1 to produce sMMO if it is desired to oxidize a wide range of VOCs. It will be useful, in some embodiments, to cause most MMO microorganisms 4 in bioreactor 1 to produce pMMO if it is desired that a relatively narrow range of VOCs are oxidized by methane monooxygenase. In particular, if the long-term growth capacity of MMO microorganisms 4 exposed to compound 5 in bioreactor 1 is a priority, than it may be useful to increase the concentration of copper in medium 2 in order to cause MMO microorganisms 4 to produce pMMO and thereby limit the bacteriocidal and/or bacteriostatic impact of compound 5 on MMO microorganisms 4. Conversely, if the oxidation of a wide variety of compounds 5 is a priority, it may be useful to decrease the concentration of copper in medium 2 in order to cause MMO microorganisms 4 to produce sMMO and thereby oxidize a wider range of compound 5. Soluble or particulate methane monooxygenase may be harvested using any well known methane monooxygenase extraction and purification method, whereby either sMMO or pMMO may be added into bioreactor 1. Controlling the concentration of iron in medium 2 may also be useful for controlling the type of MMO produced by MMO microorganisms 4, since it is known that iron concentrations also affect the capacity of methane-oxidizing microorganisms to produce MMO.

Some preferred embodiments of the invention are particularly advantageous because they meet two important parameters for the production of PHA, particularly in a non-sterile system, namely product consistency and stable system performance. The regulation of copper concentrations within medium 2 can, in one or more embodiments of the invention, be used in order to attain product consistency and stable system performance wherein non-methane organic compounds that are bacteriocidal or bacteriostatic to methane-oxidizing microorganisms are present. Specifically, the bacteriocidal and/or bacteriostatic impact of compound 5 on MMO microorganisms 4 can be mitigated by narrowing the substrate specificity of the methane monoxygenase employed in the system via the production of pMMO, as described above. The promotion of pMMO production may be used to promote system stability where the type of compound 5 employed in the system is variable, as may occur in a VOC or methane emissions stream. Alternatively, the promotion of sMMO production may be useful for the oxidation of a wider range of compound 5, which may be useful for, among other things, mitigating the bacteriocidal or bacteriostatic impact of various non-oxidized VOCs present in medium 2. The promotion of sMMO production may also be useful, in one embodiment of the invention, for the conversion of a relatively wider range of compound 5 into PHA.

In one embodiment of the invention, one or more VOCs 5 are then injected or otherwise introduced into bioreactor 1, whereby MMO microorganisms 4 within bioreactor 1 use methane monooxygenase or another enzyme suitable for the oxidation of both methane and one or more compounds 5 to catalyze the oxidation of one or more compounds 5 into one or more MMO-oxidized forms of compound 5, which are subsequently transmitted into medium 2.

In one embodiment, the MMO microorganisms include, but are not limited to, yeast, fungi, and bacteria.

Suitable yeasts include, but are not limited to, species from the genera *Candida, Hansenula, Torulopsis, Saccharomyces, Pichia,* 1-*Debaryomyces, Lipomyces, Cryptococcus, Nematospora,* and *Brettanomyces.* The preferred genera include *Candida, Hansenula, Torulopsis, Pichia,* and *Saccharomyces.* Examples of suitable species include, but are not limited to: *Candida boidinii, Candida mycoderma, Candida utilis, Candida stellatoidea, Candida robusta, Candida claussenii, Candida rugosa, Brettanomyces petrophilium, Hansenula minuta, Hansenula saturnus, Hansenula californica, Hansenula mrakii, Hansenula silvicola, Hansenula polymorpha, Hansenula wickerhamii, Hansenula capsulata, Hansenula glucozyma, Hansenula henricii, Hansenula nonfermentans, Hansenula philodendra, Torulopsis candida, Torulopsis bolmii, Torulopsis versatilis, Torulopsis glabrata, Torulopsis molishiana, Torulopsis nemodendra, Torulopsis nitratophila, Torulopsis pinus, Pichia farinosa, Pichia polymorpha, Pichia membranaefaciens, Pichia pinus, Pichia pastoris, Pichia trehalophila, Saccharomyces cerevisiae, Saccharomyces fragilis, Saccharomyces rosei, Saccharomyces acidifaciens, Saccharomyces elegans, Saccharomyces rouxii, Saccharomyces lactis,* and/or *Saccharomyces fractum.*

Suitable bacteria include, but are not limited to, species from the genera *Bacillus, Mycobacterium, Actinomyces, Nocardia, Pseudomonas, Methanomonas, Protaminobacter, Methylococcus, Arthrobacter, Methylomonas, Brevibacterium, Acetobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus,* and *Methylocystis.* Preferred genera include *Bacillus, Pseudomonas, Protaminobacter, Micrococcus, Arthrobacter* and/or *Corynebacterium.* Examples of suitable species include, but are not limited to: *Bacillus subtilus, Bacillus cereus, Bacillus aureus, Bacillus acidi, Bacillus urici, Bacillus coagulans, Bacillus mycoides, Bacillus circulans, Bacillus megaterium, Bacillus licheniformis, Pseudomonas ligustri, Pseudomonas orvilla, Pseudomonas methanica, Pseudomonas fluorescens, Pseudomonas aeruginosa, Pseudomonas oleovorans, Pseudomonas putida, Pseudomonas boreopolis, Pseudomonas pyocyanea, Pseudomonas methylphilus, Pseudomonas brevis, Pseudomonas acidovorans, Pseudomonas methanoloxidans, Pseudomonas aerogenes, Protaminobacter ruber, Corynebacterium simplex, Corynebacterium hydrocarbooxydans, Corynebacterium alkanum, Corynebacterium oleophilus, Corynebacterium hydrocarboclastus, Corynebacterium glutamicum, Corynebacterium viscosus, Corynebacterium dioxydans, Corynebacterium alkanum, Micrococcus cerificans, Micrococcus rhodius, Arthrobacter rufescens, Arthrobacter parafficum, Arthrobacter citreus, Methanomonas methanica, Methanomonas methanooxidans, Methylomonas agile, Methylomonas albus, Methylomonas rubrum, Methylomonas methanolica, Mycobacterium rhodochrous, Mycobacterium phlei, Mycobacterium brevicale, Nocardia salmonicolor, Nocardia minimus, Nocardia corallina, Nocardia butanica, Rhodopseudomonas capsulatus, Microbacterium ammoniaphilum, Archromobacter coagulans, Brevibacterium butanicum, Brevibacterium roseum, Brevibacterium flavum, Brevibacterium lactofermentum, Brevibacterium paraffinolyticum, Brevibacterium ketoglutamicum,* and/or *Brevibacterium insectiphilium.*

In some embodiments, both yeast and bacteria are used. In other embodiments, several species of either yeast or bacteria are used. In yet other embodiments, a single yeast or bacteria species is used. In other embodiments, yeast, bacteria, and/or fingi are used.

According to one embodiment, PHA microorganisms 6 (e.g., microorganisms that are capable of using the MMO-oxidized form of compound 5 as a source of carbon for growth and PHA synthesis) are introduced into bioreactor 1. In one embodiment of the invention, materials or gases comprising cultures of one or more PHA microorganisms 6 are injected into bioreactor 1 as the concentration of the MMO-oxidized form of compound 5 increases as MMO-microorganisms 4 oxidize compound 5 into the MMO-oxidized form of compound 5. In a preferred embodiment of the invention, the addition of PHA microorganisms into bioreactor 1 can be initiated simultaneous with the addition of compound 5 into bioreactor 1. In another preferred embodiment of the invention, the addition of PHA microorganisms 4 into bioreactor 1 can be initiated prior to the addition of compound 5 into bioreactor 1. In another embodiment of the invention, PHA microorganisms 6 can be injected into bioreactor 1 once the concentration of the MMO-oxidized form of compound 5 meets or exceeds 10 parts per million as a percentage by weight of medium 2, which can be measured by using one or more of a number of well known materials analysis methods, including gas chromatography. In another embodiment of the invention, PHA microorganisms 6 can be injected into bioreactor 1 once the concentration of the MMO-oxidized form of compound 5 exceeds 1 ppm. In another embodiment of the invention, PHA microorganisms 6 can be injected into bioreactor 1 once the concentration of the MMO-oxidized form of compound 5 exceeds 100 ppm.

In one embodiment, after the addition of the PHA microorganisms 6, the MMO-oxidized form of compound 5 is used by PHA microorganisms 6 as a source of carbon for cellular growth. In one embodiment, the PHA microorganisms include one or more microorganisms within the following genera: *Alcaligenes, Acidovorax, Azotobacter, Bacillus, Brevibacillus, Pseudomonas, Ralstonia, Rhizobium,* and/or *Rhodobacter.* PHA microorganisms 6 may also include an undefined microorganism conglomerate generated through the use of MMO-oxidized compound 5 as a source of carbon. PHA microorganisms may be cultivated together with heterotrophic microorganisms growing in association with the presence of organic metabolites of methane oxidation that have been transmitted into medium 2 by MMO microorganisms 4.

Once the concentration of PHA microorganisms 6 in bioreactor 1 has reached a desired concentration, at least one essential growth nutrient within medium 2, such as iron, oxygen, nitrogen, magnesium, potassium, or phosphorus, is caused to be substantially depleted while all other conditions are caused to remain substantially unchanged, thereby causing PHA microorganisms 6 to convert the carbon contained within the MMO-oxidized form of compound 5 into PHA. The PHA is then harvested according to methods known in the art.

In one embodiment, at least one essential nutrient is depleted when the PHA microorganism concentration reaches about 1 g per liter of the volume of medium 2. In another embodiment of the invention, at least one essential nutrient is depleted when the PHA microorganism concentration reaches about 0.1-10 g per liter of the volume of medium 2 (e.g., when the concentration reaches 0.1, 0.5, 2.5, 5.0, 7.5, or 10 g/l). In another embodiment of the invention, at least one essential nutrient is depleted when the PHA microorganism concentration reaches about 0.5-1 mg per liter of the volume of medium 2 (e.g., when the concentration reaches 0.5, 0.6, 0.7, 0.8, 0.9, or 1 mg/l). The PHA microorganism concentration may be determined through methods known in the art, including online turbidity measurements, batch aliquot sampling, or gas chromatographic analysis of medium 2 and/or the headspace gases of bioreactor 1.

In one embodiment, depletion of one or more essential nutrients is depleted by causing, facilitating, or allowing one or more essential nutrients to be substantially depleted by PHA microorganisms 6 and/or MMO microorganisms 4 and/or using a new growth medium devoid of one or more essential nutrients. In another embodiment, one or more essential nutrients are added independently into medium 2, such that the addition of one or more essential nutrients can be preferentially curtailed in order to induce PHA microorganisms to convert compound 5 into PHA. Thus, in some embodiments, one or more nutrients are depleted in the sense that they are used by the microorganisms and not replenished. In other embodiments, a growth medium lacking the nutrient(s) is substituted for the original medium. In yet other embodiments, essential nutrients are withheld.

In one embodiment, one or more essential nutrients are removed while all other conditions are caused to remain substantially unchanged. In alternative embodiments, one of skill in the art will appreciate that the alteration of one or more conditions that either have no impact or a positive impact on the conversion of the carbon contained within the MMO-oxidized form of compound 5 into PHA is within the scope of the invention.

In one embodiment of the invention, PHA is produced in a quantity or concentration in a range of about 0.25-0.75 kg PHA per 1 kg compound 5, wherein PHA comprises 1-75% of PHA microorganisms 6 by weight. In some embodiments, the mass or density ratio of PHA produced to VOCs added will be 1:10, 1:8, 1:6, 1:4, 1:2, or 1:1. In some embodiments, the mass or density ratio of PHA produced to microorganisms added will be 1:100, 1:75, 1:50, 1:25, 1:10, 1:5, 1:2, or 1:1.

In some embodiments, the temperature of the bioreactor can be adjusted to increase the efficiency or the quantity of PHA production.

In several embodiments, the invention comprises a PHA. In one embodiment, the PHA comprises a carbon derived from an oxidized non-methane VOC, wherein the oxidized non-methane VOC is an oxidized product (e.g., form) of a methane oxidizing microorganism. In one embodiment, one or more of the carbons in the PHA is the same as, substantially the same as, or derived from, a carbon in a non-methane VOC, and the oxidized form of that non-methane VOC. In yet another embodiment of the invention, a PHA material comprising a carbon molecule from a non-methane VOC is provided. By way of a non-limiting example, if the carbon molecules were to be labeled in a non-methane VOC, at least one of the labeled carbon molecules would appear in the final PHA product. In several embodiments, the invention comprises a PHA produced by any of the systems or methods described herein.

As used herein, volatile organic compounds(s), VOCs or non-methane VOCs shall be used interchangeably, shall be given their ordinary meaning and shall exclude or substantially exclude methane-containing compounds. VOCs shall include, but not be limited to, highly evaporative, carbon-based chemical substances; chemical compounds that evaporate readily at room temperature and contain carbon; and/or compounds comprising carbon which participate in atmospheric photochemical reactions. VOCS shall also include, but not be limited to one or more of the following: hydrocarbons (for example benzene and toluene), halocarbons, and oxygenates, and shall also specifically include, but not be limited to, one or more of the following: methylene chloride (dichloromethane); ethane; 1,1,1-trichloroethane(methyl chloroform); 1,1,2-trichloro-1,2,2-trifluoroethane (CFC-113); trichlorofluoromethane (CFC-11); dichlorodifluoromethane (CFC-12); chlorodifluoromethane (HCFC-22); trifluoromethane (HFC-23); 1,2-dichloro 1,1,2,2-tetrafluoroethane (CFC-114); chloropentafluoroethane (CFC-115); 1,1,1-trifluoro 2,2-dichloroethane (HCFC-123); 1,1,1,2-tetrafluoroethane (HFC-134a); 1,1-dichloro 1-fluoroethane (HCFC-141b); 1-chloro 1,1-difluoroethane (HCFC-142b); 2-chloro-1,1,1,2-tetrafluoroethane (HCFC-124); pentafluoroethane (HFC-125); 1,1,2,2-tetrafluoroethane (HFC-134); 1,1,1-trifluoroethane (HFC-143a); 1,1-difluoroethane (HFC-152a); parachlorobenzotrifluoride (PCBTF); cyclic, branched, or linear completely methylated siloxanes; acetone; perchloroethylene (tetrachloroethylene); propane; 3,3-dichloro-1,1,1,2,2-pentafluoropropane (HCFC-225ca); 1,3-dichloro-1,1,2,2,3-pentafluoropropane (HCFC-225cb); 1,1,1,2,3,4,4,5,5,5-decafluoropentane (HFC 43-10mee); difluoromethane (HFC-32); ethylfluoride (HFC-161); 1,1,1,3,3,3-hexafluoropropane (HFC-236fa); 1,1,2,2,3-pentafluoropropane (HFC-245ca); 1,1,2,3,3-pentafluoropropane (HFC-245ea); 1,1,1,2,3-pentafluoropropane (HFC-245eb); 1,1,1,3,3-pentafluoropropane (HFC-245fa); 1,1,1,2,3,3-hexafluoropropane (HFC-236ea); 1,1,1,3,3-pentafluorobutane (HFC-365mfc); chlorofluoromethane (HCFC-31); 1 chloro-1-fluoroethane (HCFC-151a), 1,2-dichloro-1,1,2-trifluoroethane (HCFC-123a); butane; 1,1,1,2,2,3,3,4,4-nonafluoro-4-methoxy-butane (C4F9OCH3); 2-(difluoromethoxymethyl)-1,1,1,2,3,3,3-heptafluoropropane ((CF3)2CFCF2OCH3); 1-ethoxy-1,1,2,2,3,3,4,4,4-nonafluorobutane (C4F9OC2H5); 2-(ethoxydifluoromethyl)-1,1,1,2,3,3,3-heptafluoropropane ((CF3)2CFCF2OC2H5); methyl acetate and perfluorocarbon compounds which fall into these classes: (i) Cyclic, branched, or linear, completely fluorinated alkanes; (ii) Cyclic, branched, or linear, completely fluorinated ethers with no unsaturations; (iii) Cyclic, branched, or linear, completely fluorinated tertiary amines with no unsaturations; and (iv) Sulfur containing perfluorocarbons with no unsaturations and with sulfur bonds only to carbon and fluorine. [US EPA in the Code of Federal Regulations (CFR), 40 CFR Part 51.100(s).] Methane VOCs, which may be used in some embodiments, shall include VOCs that comprise a methane chemical group.

The term polyhydroxyalkanoate (PHA) as used herein shall be given its ordinary meaning and shall include, but not be limited to, polymers generated by microorganisms as energy storage vehicles; biodegradable and biocompatible polymers that can be used as alternatives to petrochemical-based plastics such as polypropylene, polyethylene, and polystyrene; polymers produced in nature by bacterial fermentation of sugar or lipids; and/or thermoplastic or elastomeric materials derived from microorganisms. PHAs include, but are not limited to, poly-beta-hydroxybutyrate (PHB), polyhydroxyvalerate (PHV), polyhydroxybutyrate-covalerate (PHB/V), and polyhydroxyhexanoate (PHH).

The phrase "methane-oxidizing microorganisms" as used herein shall be given its ordinary meaning and shall include naturally-occurring and/or genetically-engineered microorganisms such as bacteria, fungi, or yeast, and any structural or functional equivalents, that can oxidize or otherwise metabolize methane and, in preferred embodiments, one or more VOCs. Methane-oxidizing microorganisms include "MMO microorganisms," "microorganisms synthesizing MMO," and/or "microorganisms containing MMO", which include naturally-occurring and/or genetically-engineered microorganisms, including methanotrophic, or methane-oxidizing, microorganisms, including but not limited to bacteria, fungi, or yeast, that can oxidize methane and VOCs through metabolic processes associated with methane monooxygenase, but are unable to efficiently use VOCs as their primary source of carbon and energy for growth and PHA synthesis.

The phrase "PHA microorganisms", "PHA synthesizing microorganisms", or "PHA-generating microorganisms" as used herein shall be given their ordinary meaning and shall refer to naturally-occurring and/or genetically engineered microorganisms, including but not limited to bacteria, fungi, or yeast, and any structural or functional equivalents. PHA microorganisms", "PHA synthesizing microorganisms", or "PHA-generating microorganisms" also include microorganisms that can use MMO-oxidized volatile organic compounds, that is, volatile organic compounds that have been fully or partially oxidized by methane monooxygenase, or other oxidized VOCs, as a source of carbon for growth and intracellular PHA synthesis.

The phrases "growth-culture medium" and "growth medium" as used herein shall be given their ordinary meaning and shall refer to materials affecting the growth, metabolism, PHA synthesis, and/or reproductive activities of microorganisms. One example of a growth-culture medium, and constituents thereof, useful in some preferred embodiments of the present invention include a mineral salts medium, which may comprise water, nitrogen, vitamins, iron, phosphorus, magnesium, and various other nutrients suitable to effect, support, alter, modify, control, constrain, and/or otherwise influence the metabolism and metabolic orientation of microorganisms. A growth-culture medium may comprise water filled with a range of mineral salts. For example, each liter of a liquid growth-culture medium may be comprised of about 0.7-1.5 g $KH_2PO_4$, 0.7-1.5 g $K_2HPO_4$, 0.7-1.5 g $KNO_3$, 0.7-1.5 g NaCl, 0.1-0.3 g $MgSO_4$, 24-28 mg $CaCl_2*2H_2O$, 5.0-5.4 mg EDTA $Na_4(H_2O)_{2, 1.3}$-1.7 mg $FeCl_2*4H_2O$, 0.10-0.14 mg $CoCl_2*6H_2O$, 0.08-1.12 mg $MnCl_2*2H_2O$, 0.06-0.08 mg $ZnCl_2$, 0.05-0.07 mg $H_3BO_3$, 0.023-0.027 mg $NiCl_2*6H_2O$, 0.023-0.027 mg $NaMoO_4*2H_2O$, and 0.011-0.019 mg $CuCl_2*2H_2O$. A growth-culture medium can be of any form, including a liquid, semi-liquid, gelatinous, gaseous, or solid substrate.

In one preferred embodiment, the invention comprises a novel method for the production of PHA through the use of growth-inhibiting VOCs as a source of carbon. Additional methods that can be used to carry out a process in accordance with embodiments of the invention are also provided. In particular, there are a number of methods that can be used to convert the carbon contained within growth-inhibiting VOCs into PHA material through the use of microorganisms containing methane monooxygenase, wherein methane monooxygenase is employed to convert VOCs into an MMO-oxidized carbon substrate that is subsequently used for the synthesis of polyhydroxyalkanoic acids. In some embodiments, methane monooxygenase is the sole or primary enzyme used by the microorganisms. In other embodiments, one or more enzymes are used instead of or in addition to methane monooxygenase. In some embodiments, structural and/or functional equivalents of methane monooxygenase are used.

In some embodiments, the invention comprises the use of microorganisms that are either naturally-occurring or genetically engineered.

Such methods might also include extracting methane monooxygenase from methanotrophic microorganisms prior to the conversion of VOCs into MMO-oxidized VOCs, whereby extracellular MMO is used to convert VOCs into MMO-oxidized VOCs that may be used for PHA production. As with intracellular methane monooxygenase, extracellular enzymatic reaction may comprise the use of methane monooxygenase and/or other enzymes that can oxidize VOCs or metabolize VOCS to produce an oxidized VOC compound that can be used by PHA microorganisms as a source of carbon. In one embodiment, synthetic MMO, or a structural and/or functional MMO equivalent is used for extracellular or in vitro processing (e.g., oxidation) of VOCs.

In some embodiments, the invention comprises adding additional carbon sources into the growth medium in order to influence the metabolism of the microorganisms, such as chemicals that are known to cause some microorganisms to alter the molecular structure of PHA molecules, such as valeric acid.

In other embodiments, the invention comprises using VOCs contained within industrial gases such as landfill gas, natural gas, agricultural digester gas, agricultural emissions gas, and/or wastewater treatment gas as a source of carbon for PHA production.

In yet other embodiments, the invention comprises growing methanotrophic microorganisms prior to or in simultaneous conjunction with the mutual-exposure of VOCs and methanotrophic microorganisms.

In any case, the detailed description of the preferred method of carrying out a process in accordance with the invention should serve foremost as an elucidation of the technical feasibility of carrying out the invention, rather than as a limitation of the process of the invention itself.

Accordingly, the reader will see that the invention, by providing a process for the novel use of volatile organic compounds as a source of carbon for PHA production, provides a process which i) converts a growth-limiting substrate into a useful source of carbon for PHA production, ii) converts an environmental toxin into a non-toxic and useful good, iii) creates an environmentally-friendly good in the form of biodegradable thermoplastic from a heretofore wasted and environmentally-damaging industrial byproduct, iv) uses a material previously considered non-useful for PHA production, v) reduces the cost of PHA production while improving the environment, and vi) increases the economic viability of PHA plastics relative to petrochemical-based plastics.

The following example describes one non-limiting embodiment of the invention.

EXAMPLE 1

In one embodiment of a method to carry out a process in accordance with one embodiment of the invention, as pictured in FIG. 1, bioreactor 1 is partially filled with liquid mineral water growth medium 2 comprising, per liter of water, 0.7-1.5 g $KH_2PO_4$, 0.7-1.5 g $K_2HPO_4$, 0.7-1.5 g $KNO_3$, 0.7-1.5 g NaCl, 0.1-0.3 g $MgSO_4$, 24-28 mg CaCl2*2H2O, 5.0-5.4 mg EDTA Na4(H2O)$_{2, 1.3}$-1.7 mg FeCl2*4H2O, 0.10-0.14 mg CoCl2*6H2O, 0.08-1.12 mg MnCl2*2H2O, 0.06-0.08 mg ZnCl2, 0.05-0.07 mg H3BO3, 0.023-0.027 mg NiCl2*6H2O, 0.023-0.027 mg NaMoO4*2H2O, and 0.011-0.019 mg CuCl2*2H2O, Next, air 3 comprising 50% methane and 50% oxygen (by volume) is injected into the liquid portion of bioreactor 1. Next, MMO microorganisms 4 are introduced to bioreactor 1 and caused to propogate through the use of the methane within air 3 as a source of carbon for growth. Volatile organic compound 5 is then injected into bioreactor 1, whereby MMO microorganisms 4 within bioreactor 1 use methane monooxygenase to catalyze the oxidation of compound 5 into one or more MMO-oxidized forms of compound 5, which are subsequently transmitted into medium 2. Next, PHA microorganisms 6, that is, microorganisms that are capable of using the MMO-oxidized form of compound 5 as a source of carbon for growth and PHA synthesis, are introduced into bioreactor 1, whereby the MMO-oxidized form of compound 5 is used by PHA microorganisms 6 as a source of carbon for cellular growth. Once the concentration of PHA microorganisms 6 in bioreactor 1 has reached a desired concentration, at least one essential growth nutrient within medium 2, such as iron, oxygen, nitrogen, magnesium, potassium, or phosphate, is caused to be substantially depleted while all other conditions are caused to remain substantially unchanged, thereby causing PHA microorganisms 6 to convert the carbon contained within the MMO-oxidized form of compound 5 into PHA.

While the above descriptions of methods of carrying out a process in accordance with the invention contains many specificities, these should not be construed as limitations on the scope of the invention. As stated, there are a number of ways to carry out a process in accordance with the invention. Accordingly, the scope of the invention should be determined not by the preferred method described, but by the appended claims and their legal equivalents.

What is claimed is:

1. A process for the production of a polyhydroxyalkanoate (PHA) from one or more metabolically toxic and growth-inhibiting volatile organic compounds (VOCS), comprising:
    a) providing one or more non-methane VOCs;
    b) providing one or more first microorganisms capable of oxidizing said one or more VOCs to produce an oxidized compound, wherein said first microorganisms are methane-oxidizing microorganisms, and wherein said one or more first microorganisms do not use said one or more VOCs as a source of carbon or energy, and wherein said one or more VOCs inhibits the growth of said one or more first microorganisms, and is thereby metabolically toxic;
    c) providing one or more second microorganisms capable of incorporating a carbon contained within said oxidized compound into a PHA material, wherein said second microorganisms are PHA-synthesizing microorganisms;
    d) providing a growth-culture medium that regulates the metabolism of said one or more first microorganisms and said one or more second microorganisms;
    e) exposing said one or more first microorganisms in said growth-culture medium to said one or more VOCs, thereby causing or allowing said one or more first microorganisms to convert said one or more VOCS into said oxidized compound;
    f) increasing the availability of copper to said one or more first microorganisms, thereby causing said one or more first microorganisms to produce particulate methane monooxygenase;
    g) contacting said oxidized compound with said second microorganisms; and
    h) manipulating said growth-culture medium to cause or allow said one or more second microorganisms to use said carbon contained within said oxidized compound for the production of said PHA material, thereby using a metabolically toxic, growth-inhibiting VOC to produce said PHA material.

2. The method of claim 1, further comprising exposing said one or more first microorganisms to methane prior to exposing said one or more first microorganisms to said VOCS to encourage growth of said first microorganisms.

3. The method of claim 1, wherein said one or more VOCs are obtained from one or more of the following sources: landfill, wastewater treatment system, coal mine, natural gas system, agricultural waste management system, and ruminant animal operation.

4. The method of claim 1, wherein said one or more VOCs are selected from the group consisting of one or more of the following compounds: vinyl chloride, benzene, butane, trichloroethylene, toluene, ethylbenzene, dichloromethane, trichloromethane, ethane, 1-2-dichloroethane, 1,1-dichloroethylene, chlorodifluoromethane, and xylene.

5. The method of claim 1, wherein said one or more first microorganisms comprise one or more methane monooxygenases (MMOs), and wherein said one or more VOCs inhibit the growth of said first microorganisms by temporarily or permanently deactivating said one or more MMOs.

6. The method of claim 1, wherein said one or more VOCs inhibit the growth of said first microorganisms by exhibiting bacteriocidal or bacteriostatic activity.

7. The method of claim 1, wherein said one or more first microorganisms comprise a naturally-occurring microorganism capable of oxidizing said one or more VOCs.

8. The method of claim 1, wherein said one or more first microorganisms oxidize said one or more VOCs using methane monooxygenase.

9. The method of claim 1, wherein said one or more first microorganisms are selected from one or more genera selected from the group consisting of *Bacillus, Mycobacterium, Actinomyces, Nocardia, Pseudomonas, Methanomonas, Protaminobacter, Methylococcus, Arthrobacter, Methylomonas, Brevibacterium, Acetobacter, Methylomonas, Brevibacterium, Micrococcus, Rhodopseudomonas, Corynebacterium, Rhodopseudomonas, Microbacterium, Achromobacter, Methylobacter, Methylosinus*, and *Methylocystis*.

10. The method of claim 1, wherein said one or more second microorganisms comprise a naturally-occurring microorganism capable of using carbon from said oxidized compound to produce said PHA material.

11. The method of claim 1, wherein said one or more second microorganisms are selected from one or more genera selected from the group consisting of: *Alcaligenes, Acidovorax, Azotobacter, Bacillus, Brevibacillus, Pseudomonas, Ralstonia, Rhizobium*, and *Rhodobacter*.

12. The method of claim 1, wherein said growth-culture medium comprises one or more of the following: potassium, phosphorus, nitrogen, magnesium, sulfate, iron, cobalt, copper, dissolved oxygen, dissolved methane, dissolved VOCs, zinc, sodium, nickel, manganese, boron, water, microorganisms, and organic metabolites.

13. The method of claim 1, wherein manipulating said growth-culture medium to cause or allow said one or more second microorganisms for the production of said PHA material comprises depleting an essential growth nutrient.

14. The method of claim 1, wherein manipulating said growth-culture medium to cause or allow said one or more second microorganisms to produce said PHA material comprises reducing the concentration of one or more of the following selected from the group consisting of: iron, oxygen, nitrogen, magnesium, potassium, and phosphate.

15. The method of claim 1, wherein said PHA material comprises at least one carbon molecule derived from said oxidized compound, wherein said oxidized compound is the oxidized form of said one or more VOCs.

16. The method of claim 1, further comprising harvesting said PHA material.

17. The method of claim 1, wherein the mass of PHA material produced is about 5-80% of the mass of said second microorganisms used to produce said PHA material.

18. The method of claim 1, wherein the mass of PHA material produced is greater than 50% of the mass of said second microorganisms used to produce said PHA material.

19. The method of claim 1, further comprising altering the concentration of one or more compounds within said growth culture medium to alter the substrate specificity of methane monooxygenase.

20. The method of claim 19, wherein said one or more compounds comprises iron.

21. A process for the production of a polyhydroxyalkanoate (PHA) from one or more metabolically toxic and growth-inhibiting volatile organic compounds (VOCS), comprising:
   a) providing one or more non-methane VOCs;
   b) providing one or more genetically engineered first microorganisms capable of oxidizing said one or more VOCs to produce an oxidized compound, wherein said first microorganisms are methane-oxidizing microorganisms, wherein said one or more first microorganisms do not use said one or more VOCs as a source of carbon or energy, and wherein said one or more VOCs inhibits the growth of said one or more first microorganisms, and is thereby metabolically toxic;
   c) providing one or more second microorganisms capable of incorporating a carbon contained within said oxidized compound into a PHA material, wherein said second microorganisms are PHA-synthesizing microorganisms;
   d) providing a growth-culture medium that regulates the metabolism of said one or more first microorganisms and said one or more second microorganisms;
   e) exposing said one or more first microorganisms in said growth-culture medium to said one or more VOCs, thereby causing or allowing said one or more first microorganisms to convert said one or more VOCS into said oxidized compound;
   f) increasing the availability of copper to said one or more first microorganisms, thereby causing said one or more first microorganisms to produce particulate methane monooxygenase;
   g) contacting said oxidized compound with said second microorganisms; and
   h) manipulating said growth-culture medium to cause or allow said one or more second microorganisms to use said carbon contained within said oxidized compound for the production of said PHA material, thereby using a metabolically toxic, growth-inhibiting VOC to produce said PHA material.

22. A process for the production of a polyhydroxyalkanoate (PHA) from one or more metabolically toxic and growth-inhibiting volatile organic compounds (VOCS), comprising:
   a) providing one or more non-methane VOCs;
   b) providing one or more first microorganisms capable of oxidizing said one or more VOCs to produce an oxidized compound, wherein said first microorganisms are methane-oxidizing microorganisms, wherein said one or more first microorganisms do not use said one or more VOCs as a source of carbon or energy, and wherein said one or more VOCs inhibits the growth of said one or more first microorganisms, and is thereby metabolically toxic;
   c) providing one or more genetically engineered second microorganisms capable of incorporating a carbon contained within said oxidized compound into a PHA material, wherein said second microorganisms are PHA-synthesizing microorganisms;
   d) providing a growth-culture medium that regulates the metabolism of said one or more first microorganisms and said one or more second microorganisms;
   e) exposing said one or more first microorganisms in said growth-culture medium to said one or more VOCs, thereby causing or allowing said one or more first microorganisms to convert said one or more VOCS into said oxidized compound;
   f) increasing the availability of copper to said one or more first microorganisms, thereby causing said one or more first microorganisms to produce particulate methane monooxygenase;
   g) contacting said oxidized compound with said second microorganisms; and
   h) manipulating said growth-culture medium to cause or allow said one or more second microorganisms to use said carbon contained within said oxidized compound for the production of said PHA material, thereby using a metabolically toxic, growth-inhibiting VOC to produce said PHA material.

* * * * *

UNITED STATES PATENT AND TRADEMARK OFFICE
CERTIFICATE OF CORRECTION

PATENT NO. : 7,579,176 B2
APPLICATION NO. : 11/676928
DATED : August 25, 2009
INVENTOR(S) : Markus Herrema and Kenton Kimmel It is certified that error appears in the above-identified patent and that said Letters Patent is hereby corrected as shown below:

Column 1, Line 20-21, delete "polyhydroxyalknoic acid" and insert --polyhydroxyalkanoic acid--, therefor.

Column 4, Line 36-37, delete "growth culture" and insert --growth-culture--, therefor.

Column 7, Line 40-41 (Approx.), delete "1-2- dichloroethane" and insert --1,2-dichloroethane--, therefor.

Column 7, Line 51, After "Corynebacterium," delete "Rhodopseudomonas," therefor.

Column 8-9, Line 64-67 and Line 1-4,
Delete "0.7-1.5 g KH2PO4, 0.7-1.5 g K2HPO4, 0.7-1.5 g KNO3, 0.7-1.5 g NaCl, 0.1-0.3 g MgSO4, 24-28 mg CaCl2*2H2O, 5.0-5.4 mg EDTA Na4(H2O)2, 1.3-1.7 mg FeCl2*4H2O, 0.10-0.14 mg CoCl2*6H2O, 0.08-1.12 mg MnCl2*2H2O, 0.06-0.08 mg ZnCl2, 0.05-0.07 mg H3BO3, 0.023-0.027 mg NiCl2*6H2O, 0.023-0.027 mg NaMoO4*2H2O, and 0.011-0.019 mg CuCl2*2H2O." and insert --0.7-1.5 g $KH_2PO_4$, 0.7-1.5 g $K_2HPO_4$, 0.7-1.5 g $KNO_3$, 0.7-1.5 g NaCl, 0.1-0.3 g $MgSO_4$, 24-28 mg $CaCl_2*2H_2O$, 5.0-5.4 mg EDTA $Na_4(H_2O)2$, 1.3-1.7 mg $FeCl_2*4H_2O$, 0.10-0.14 mg $CoCl_2*6H_2O$, 0.08-1.12 mg $MnCl_2*2H_2O$, 0.06-0.08 mg $ZnCl_2$, 0.05-0.07 mg $H_3BO_3$, 0.023-0.027 mg $NiCl_2*6H_2O$, 0.023-0.027 mg $NaMoO_4*2H_2O$, and 0.011-0.019 mg $CuCl_2*2H_2O$."--, therefor.

Column 11, Line 51, delete "Bacillus subtilus" and insert --Bacillus subtilis--, therefor.

Column 12, Line 7, delete "Archromobacter" and insert --Achromobacter--, therefor.

Column 12, Line 16 (Approx), Delete "fingi" and insert --fungi--, therefor.

Column 14, Line 17, delete "-trichloroethane(methyl" and insert --trichloroethane (methyl--, therefor.

Column 14, Line 42, delete "1 chloro" and insert --1 –chloro--, therefor.

Column 14, Line 44, delete "(C4F9OCH3);" and insert --($C_4F_9OCH_3$);--, therefor.

Signed and Sealed this
Twelfth Day of April, 2011

David J. Kappos
*Director of the United States Patent and Trademark Office*

CERTIFICATE OF CORRECTION (continued)
U.S. Pat. No. 7,579,176 B2

Column 14, Line 46, delete "((CF3)2CFCF2OCH3);" and insert --((CF$_3$)$_2$CFCF$_2$OCH$_3$);--, therefor.

Column 14, Line 47, delete "(C4F9OC2H5);" and insert --(C$_4$F$_9$OC$_2$H$_5$);--, therefor.

Column 14, Line 48-49, delete "((CF3)2CFCF2OC2H5);" and insert --((CF$_3$)$_2$CFCF$_2$OC$_2$H$_5$);--, therefor.

Column 15, Line 48-54,
Delete "0.7-1.5 g KH2PO4, 0.7-1.5 g K2HPO4, 0.7-1.5 g KNO3, 0.7-1.5 g NaCl, 0.1-0.3 g MgSO4, 24-28 mg CaCl2*2H2O, 5.0-5.4 mg EDTA Na4(H2O)2, $_{1.3}$-1.7 mg FeCl2*4H2O, 0.10- 0.14 mg CoCl2*6H2O, 0.08-1.12 mg MnCl2*2H2O, 0.06-0.08 mg ZnCl2, 0.05-0.07 mg H3BO3, 0.023-0.027 mg NiCl2*6H2O, 0.023-0.027 mg NaMoO4*2H2O, and 0.011-0.019 mg CuCl2*2H2O."
and insert --0.7-1.5 g KH$_2$PO$_4$, 0.7-1.5 g K$_2$HPO$_4$, 0.7-1.5 g KNO$_3$, 0.7-1.5 g NaCl, 0.1-0.3 g MgSO$_4$, 24-28 mg CaCl$_2$*2H$_2$O, 5.0-5.4 mg EDTA Na$_4$(H$_2$O)2, 1.3-1.7 mg FeCl$_2$*4H$_2$O, 0.10-0.14 mg CoCl$_2$*6H$_2$O, 0.08-1.12 mg MnCl$_2$*2H$_2$O, 0.06-0.08 mg ZnCl$_2$, 0.05-0.07 mg H$_3$BO$_3$, 0.023-0.027 mg NiCl$_2$*6H$_2$O, 0.023-0.027 mg NaMoO$_4$*2H$_2$O, and 0.011-0.019 mg CuCl$_2$*2H$_2$O.--, therefor.

Column 16-17, Line 66-67, and Line 1-5,
Delete "0.7-1.5 g KH2PO4, 0.7-1.5 g K2HPO4, 0.7-1.5 g KNO3, 0.7-1.5 g NaCl, 0.1-0.3 g MgSO4, 24-28 mg CaCl2*2H2O, 5.0-5.4 mg EDTA Na4(H2O)2, $_{1.3}$-1.7 mg FeCl2*4H2O, 0.10-0.14 mg CoCl2*6H2O, 0.08-1.12 mg MnCl2*2H2O, 0.06-0.08 mg ZnCl2, 0.05-0.07 mg H3BO3, 0.023-0.027 mg NiCl2*6H2O, 0.023-0.027 mg NaMoO4*2H2O, and 0.011-0.019 mg CuCl2*2H2O"
and insert --0.7-1.5 g KH$_2$PO$_4$, 0.7-1.5 g K$_2$HPO$_4$, 0.7-1.5 g KNO$_3$, 0.7-1.5 g NaCl, 0.1-0.3 g MgSO$_4$, 24-28 mg CaCl$_2$*2H$_2$O, 5.0-5.4 mg EDTA Na$_4$(H$_2$O)2, 1.3-1.7 mg FeCl$_2$*4H$_2$O, 0.10-0.14 mg CoCl$_2$*6H$_2$O, 0.08-1.12 mg MnCl$_2$*2H$_2$O, 0.06-0.08 mg ZnCl$_2$, 0.05-0.07 mg H$_3$BO$_3$, 0.023-0.027 mg NiCl$_2$*6H$_2$O, 0.023-0.027 mg NaMoO$_4$*2H$_2$O, and 0.011-0.019 mg CuCl$_2$*2H$_2$O--, therefor.

Column 17, Line 5, After "2H$_2$O" delete "," and insert --.--, therefor.

Column 18, Line 22, In Claim 4, delete "1-2-dichloroethane" and insert --1,2-dichloroethane--, therefor.

Column 18, Line 43, In Claim 9, after "Acetobacter," delete "Methylomonas,".

Column 18, Line 44, In Claim 9, before "Micrococcus," delete "Brevibacterium,".

Column 18, Line 45, In Claim 9, before "Microbacterium," delete "Rhodopseudomonas,".